United States Patent
Fairhurst et al.

(10) Patent No.: US 10,258,571 B2
(45) Date of Patent: Apr. 16, 2019

(54) DELIVERY DEVICES CONTAINING ENCAPSULATED AND/OR PRACTICE-BOUND ACTIVE PHARMACEUTICAL INGREDIENTS

(75) Inventors: David Fairhurst, Congers, NY (US); Garry Thomas Gwozdz, Nazareth, PA (US); Mark Mitchnick, East Hampton, NY (US); Abhijit Gokhale, Allentown, PA (US); Andrew Loxley, Philadelphia, PA (US)

(73) Assignee: PARTICLE SCIENCES, INC., Bethlehem, PA (US)

( * ) Notice: Subject to any disclaimer, the term of this patent is extended or adjusted under 35 U.S.C. 154(b) by 809 days.

(21) Appl. No.: 12/525,568

(22) PCT Filed: Feb. 12, 2008

(86) PCT No.: PCT/US2008/053635
§ 371 (c)(1),
(2), (4) Date: Aug. 19, 2009

(87) PCT Pub. No.: WO2008/100876
PCT Pub. Date: Aug. 21, 2008

(65) Prior Publication Data
US 2010/0034863 A1   Feb. 11, 2010

Related U.S. Application Data

(60) Provisional application No. 60/889,332, filed on Feb. 12, 2007.

(51) Int. Cl.
A61K 9/16 (2006.01)
A61K 9/00 (2006.01)
A61L 31/16 (2006.01)

(52) U.S. Cl.
CPC .......... *A61K 9/1617* (2013.01); *A61K 9/0031* (2013.01); *A61K 9/0036* (2013.01); *A61K 9/0043* (2013.01); *A61K 9/0056* (2013.01); *A61L 31/16* (2013.01)

(58) Field of Classification Search
CPC .. A61K 9/1617; A61K 9/0056; A61K 9/0043; A61K 9/0031; A61K 9/0036; A61L 31/16
See application file for complete search history.

(56) References Cited

U.S. PATENT DOCUMENTS

| | | | |
|---|---|---|---|
| 4,016,251 A | 4/1977 | Higuchi et al. | 424/432 |
| 2003/0147962 A1 | 8/2003 | Bernstein et al. | 424/486 |
| 2004/0033264 A1 | 2/2004 | Sawhney | 424/486 |
| 2005/0276836 A1 | 12/2005 | Wilson et al. | 424/422 |
| 2006/0002966 A1 | 1/2006 | Pauletti et al. | 424/422 |
| 2006/0240071 A1 | 10/2006 | Lerner et al. | 424/426 |

FOREIGN PATENT DOCUMENTS

EP  1 466 631 A1  10/2004

OTHER PUBLICATIONS

Extended Search Report from EPO Application No. 08729580.4, dated Jun. 26, 2013, EPO.
Liu et al. "Composite Hydrogels for Sustained Release of Therapeutic Agents" Soft Materials 2003 1(3):393-408.

*Primary Examiner* — Robert S Cabral
(74) *Attorney, Agent, or Firm* — Licata & Tyrrell P.C.

(57) ABSTRACT

Delivery devices of a degradable or nondegradable biocompatible matrix with one or more encapsulated active pharmaceutical ingredients or one or more particle-bound active pharmaceutical ingredients dispersed in the matrix are provided. Also provided are methods for delivering an active pharmaceutical ingredient to a subject with these delivery devices. Modified vaginal rings are also provided as well as surface coatings for delivery devices which minimize biointeraction of the coated delivery devices.

12 Claims, 1 Drawing Sheet

DELIVERY DEVICES CONTAINING ENCAPSULATED AND/OR PRACTICE-BOUND ACTIVE PHARMACEUTICAL INGREDIENTS

This patent application is the National Stage of International Application No. PCT/US2008/053535, filed Feb. 12, 2008, which claims the benefit of priority from U.S. Provisional Application Ser. No. 60/889,332, filed Feb. 12, 2007, teachings of which are herein incorporated by reference in their entirety.

FIELD OF THE INVENTION

The present invention relates to delivery devices comprising a degradable or nondegradable biocompatible matrix with an encapsulated active pharmaceutical ingredient and/or a particle-bound active pharmaceutical ingredient dispersed in the matrix, modified vaginal rings and surface coating for delivery devices which minimize bio-interactions.

BACKGROUND OF THE INVENTION

Effective delivery of an active pharmaceutical ingredient is challenging. Hydrophobic active ingredients present challenges associated with poor aqueous solubility and slow dissolution rate while hydrophilic active ingredients, though readily soluble in aqueous environments, are poorly absorbed due to membrane impermeability and/or enzymatic degradation. While separately they present a formidable challenge, delivering both in a single device is exponentially more difficult. A multitude of drug delivery devices attempting to address these challenges and provide for release of pharmaceutically active ingredients in a controlled and continuous rate for a prolonged period of time have been described.

For example, vaginal ring technologies have been described providing for a once-a-month, or once-every-three to twelve month dosing regimen. Existing vaginal ring systems are typically manufactured from silicone elastomers and/or ethylene vinyl acetate polymers. See, for example, U.S. Pat. No. 4,016,251. Release from vaginal rings is generally controlled by diffusion of the active pharmaceutical ingredient and/or erosion of the ring matrix. Manufacture of existing vaginal ring systems is fairly complex as existing rings comprise an inner reservoir or core containing the active pharmaceutical ingredient and an outer silicone elastomer or ethylene vinyl acetate polymer shell. Further, in existing rings diffusion from the core to the shell reduces the overall rate of diffusion so that extended metered release into the vaginal lumen is obtained. However, cores and shells that are amenable to passage of hydrophobic compounds are not typically amenable to passage of hydrophilic compounds. Hence, delivery of dissimilar molecules with existing ring technologies is challenging.

Accordingly, there are a number of areas in which current vaginal ring technology as well as other drug delivery devices can be improved. These include manufacturing ease, cost, multi-drug delivery, and environmental impact.

SUMMARY OF THE INVENTION

An aspect of the present invention relates to a delivery device for active pharmaceutical ingredients comprising a degradable or nondegradable biocompatible matrix and one or more encapsulated active pharmaceutical ingredients and/or one or more active pharmaceutical ingredients bound to particles. In some embodiments the matrix may also contain one or more non-encapsulated or non-particle-bound active pharmaceutical ingredients. The matrix is shaped to facilitate delivery of the active pharmaceutical ingredient to its site of therapeutic action.

Another aspect of the present invention relates to methods for production of these delivery devices and methods for their use in delivering one or more active pharmaceutical ingredients to a subject.

Another aspect of the present invention relates to a vaginal ring with a ring body having an irregular surface to increase surface area of the vaginal ring.

Yet another aspect of the present invention relates to a surface coating which minimizes bio-interaction of a delivery device for an activated pharmaceutical ingredient which comprises one or more anionic or nonionic hydrophilic polymers and which is applied as a coating to a delivery device.

DETAILED DESCRIPTION OF THE INVENTION

Figure 1:
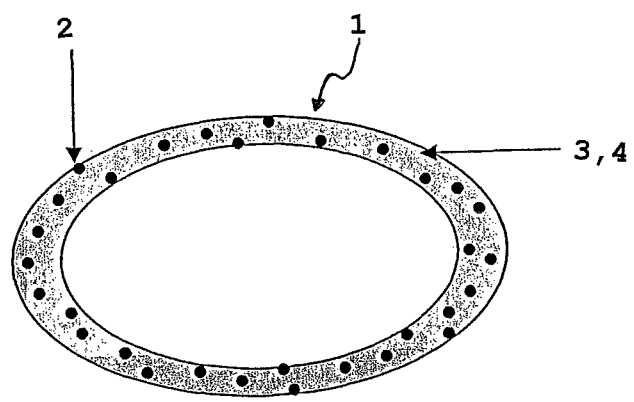
FIG. 1 is a schematic of an exemplary delivery device of the present invention. In this exemplary embodiment, the matrix is shaped as a vaginal ring and comprises encapsulated active pharmaceutical ingredients dispersed throughout the matrix ring. In this embodiment, the matrix itself contains a separate active pharmaceutical ingredient.

The present invention provides delivery devices for active pharmaceutical ingredients, methods for production of these delivery devices, and methods for use of these devices in delivering an active pharmaceutical ingredient or active pharmaceutical ingredients to a subject. The active pharmaceutical ingredient delivery devices of the present invention are easier to manufacture than existing delivery devices and provide for multi-agent delivery. Further, manufacturing costs for these devices is expected to be decreased.

The delivery devices of the present invention comprise a degradable or nondegradable biocompatible matrix. Selection of the biocompatible matrix material and its shape, as well as its degradation characteristics, is based upon the active pharmaceutical ingredient or active pharmaceutical ingredients to be delivered, the desired length of action, and the targeted site for delivery in a subject.

For example, delivery of an active pharmaceutical ingredient or active pharmaceutical ingredients to the vaginal lumen can be achieved with a nondegradable matrix material shaped as a vaginal ring or as an intra-uterine device. Exemplary matrix materials for use in this type of delivery device of the present invention include, but are in no way limited to, ethylene-vinyl acetate (EVA), silicones, waxes, lipids and hydrophilic compounds. Similar ring technologies can be used in anastomosis rings for delivery of an active pharmaceutical ingredient or active pharmaceutical ingredients to the surrounding area.

Delivery of an active pharmaceutical ingredient or active pharmaceutical ingredients to the vasculature can be achieved via a stent-shaped matrix comprising either a nondegradable matrix material similar to those described for vaginal delivery or a degradable matrix material.

Oral and/or rectal and/or nasal delivery of an active pharmaceutical ingredient or active pharmaceutical ingredients can be achieved with a delivery device of the present invention comprising a nondegradable or degradable matrix material shaped as a film. Preferably, films of the present invention are dissolvable and thus comprised of a degradable matrix material such as, but not limited to poly (ethylene) oxide or hydroxypropyl methylcellulose, singularly or in combination. Additional exemplary polymers for use in dissolvable films of the present invention are well known in the art. In this embodiment, the device may also be provided as a semisolid gel or cream which forms a film upon application.

Systemic delivery of an active pharmaceutical ingredient or active pharmaceutical ingredients for a period of weeks to months can be achieved with a delivery device of the present invention shaped for ease in implantation and comprising a nondegradable or degradable matrix material which meets therapeutic demands of the active pharmaceutical ingredient or active pharmaceutical ingredients being delivered. Exemplary shapes for systemic delivery devices of the present invention include, but are in no way limited to, rods and discs.

Long term ocular delivery of an active pharmaceutical ingredient or active pharmaceutical ingredients can also be achieved with the present invention via, for example, a lens shaped nondegradable matrix.

In addition, targeted delivery, for example, to a tumor in a subject, of an active pharmaceutical ingredient or active pharmaceutical ingredients can be achieved with the present invention via a matrix shaped to maintain its location. For example, the matrix may be rod- or disc-shaped with a barb or barbs which attach to the tumor to fix the location of the delivery device at the tumor site. In this embodiment, the matrix material is selected to meet the therapeutic demands of the active pharmaceutical ingredient or active pharmaceutical ingredients to be delivered.

By "degradable matrix" as used herein, it is meant to include matrix materials which change chemically and/or physically under physiological or environmental conditions following administration as well as matrix materials which change chemically and/or physically by intentional stimulation, for example, via ultrasound or thermal treatment, thereby releasing the active pharmaceutical ingredient or active pharmaceutical ingredients.

Delivery devices of the present invention further comprise one or more encapsulated active pharmaceutical ingredients and/or one or more particle-bound active pharmaceutical ingredients dispersed in the matrix. Encapsulated active pharmaceutical ingredients and/or active pharmaceutical ingredients bound to particles may be dispersed evenly or unevenly in the matrix.

When encapsulated, it is preferred that the active pharmaceutical ingredient or active pharmaceutical ingredients be microencapsulated, and more preferably nanoencapsulated. Thus, encapsulated active pharmaceutical ingredients used in the delivery devices of the present invention are preferably 1000 microns or less, more preferably 100 microns or less, more preferably 1 micron or less, and most preferably 0.1 micron or less in size. A preferred size range for nanoencapsulated active pharmaceutical ingredients used in the delivery devices of the present invention is 25 to 1000 nm.

Examples of encapsulation materials for the active pharmaceutical ingredient or active pharmaceutical ingredients include, but are not limited to, natural or synthetic waxes or wax-like materials such as beeswax, carnauba wax, hydrogenated vegetable oils, stearyl alcohol, and cetyl alcohol, polymeric materials such as polyethylene, polyethylene glycol, polyvinyl alcohol, and silicone polymers, naturally occurring gelling agents such as gelatin, gellan gum, carregenens, and alginates, and combinations thereof.

Various methods can used to encapsulate the active pharmaceutical ingredient or active pharmaceutical ingredients for use in the delivery devices of the present invention. For example, a melt-chill process can be used. This process comprises dissolving or dispersing the active pharmaceutical ingredient or active pharmaceutical ingredients into the encapsulation material at a temperature above the melt point of the encapsulation material, emulsifying the mixture into a non-miscible carrier using suitable emulsifying agents, cooling the emulsified mixture to form a solid, and forming particles from the solid. Alternatively, a solvent emulsification process can be used. This process comprises dissolving the active pharmaceutical ingredient or active pharmaceutical ingredients and the encapsulation material into an appropriate solvent, emulsifying the resultant mixture into a non-miscible carrier using suitable emulsifying agents, and removing the solvent to form the particles. In both the melt-chill process and the solvent emulsification process, the non-miscible carrier can be removed prior to or during processing of the encapsulated active pharmaceutical ingredient or active pharmaceutical ingredients into the delivery form, or may be a material that becomes part of the delivery form. Additional exemplary encapsulation methods suitable to forming encapsulated active pharmaceutical ingredients for use in the delivery devices of the present invention include, but are not limited to, spray-drying, which comprises dissolving or dispersing the active pharmaceutical ingredient or active pharmaceutical ingredients into the encapsulation material in a liquid state either through raising the temperature above the melt point or use of a solvent for the encapsulation material, atomizing the resultant mixture, and forming particles of encapsulated active pharmaceutical ingredient or active pharmaceutical ingredients through cooling or removal of the solvent, and by physical means, which comprises dissolving or dispersing the active pharmaceutical ingredient or active pharmaceutical ingredients into the encapsulation material using heat or solvent, solidifying the mixture by cooling or solvent removal, and then physically grinding the resulting solid material by known means to provide the desired particles of encapsulated active pharmaceutical ingredient or active pharmaceutical ingredients.

Alternatively, or in addition, the active pharmaceutical ingredient or active pharmaceutical ingredients can be bound to a particle and released as thermodynamics dictate. For example, the active pharmaceutical ingredient or active pharmaceutical ingredients can be adsorbed directly to particles of zinc oxide or attached via a coupling agent such as, but not limited to, a reactive silane, an organometallic titanate, a zirconate or an aluminate. An example of a reactive silane useful in the present invention is A1100 (Edwin P. Plueddemann in "Silane Coupling Agents", Plenum Press, New York (1982). Additional exemplary particles to which an active pharmaceutical ingredient or active pharmaceutical ingredients can be bound include, but are not limited to, wax particles and polymer particles. Particles to which an active pharmaceutical ingredient or active pharmaceutical ingredients can be bound are preferably 1000 microns or less, more preferably 100 microns or less, more preferably 1 micron or less, and most preferably 0.1 micron or less in size. A preferred size range for particles to which an active pharmaceutical ingredient or active pharmaceutical ingredients are bound is 25 to 1000 nm.

Active pharmaceutical ingredients which can be encapsulated or bound to a particle and dispersed into the matrix materials of the delivery devices of the present invention include, but are in no way limited to, drugs, including vaccines, nutritional agents, cosmeceuticals and diagnostic agents. Examples of active pharmaceutical ingredients for use in the present invention include, but are not limited to analgesics, anti-anginal agents, anti-arrhythmic agents, anti-angiogenic agents, antibacterial agents, anti-benign prostate hypertrophy agents, anti-coagulants, anti-depressants, anti-diabetic agents, anti-epileptic agents, anti-fungal agents, anti-gout agents, anti-hypertensive agents, anti-inflammatory agents, anti-malarial agents, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anxiolytics, beta-blockers, cardiac inotropic agents, cognition enhancers, corticosteroids, COX-2 inhibitors, diuretics, erectile dysfunction improvement agents, essential fatty acids, gastrointestinal agents, histamine receptor antagonists, hormones, immunosuppressants, keratolyptics, leukotriene antagonists, lipid regulating agents, macrolides, muscle relaxants, non-essential fatty acids, nutritional agents, nutritional oils, protease inhibitors and stimulants.

In some delivery devices of the present invention, one or more non-encapsulated or non-particle bound active pharmaceutical ingredient is also added to the matrix material. In fact, multiple active pharmaceutical ingredients can be encapsulated and/or bound to particles and dispersed and/or incorporated directly in the matrix. In general, an active pharmaceutical ingredient added directly to the device matrix is compatible with the matrix. Thus, if the matrix is comprised of silicone or ethylene-vinyl acetate then any active pharmaceutical ingredient added directly to the matrix is generally hydrophobic. If the matrix is comprised of a hydrophilic polymer then any active pharmaceutical ingredient added directly to matrix is generally hydrophilic.

However, it has been found that differences in the hydrophilic or hydrophobic nature of the encapsulated and/or non-particle bound active pharmaceutical ingredients dispersed in the matrix alter the release of active pharmaceutical ingredient dispersed directly to the matrix as compared to a matrix containing only the directly dispersed active pharmaceutical ingredient. For example, for a vaginal ring, it was found that encapsulating particles alone can impact release. Specifically, a ring matrix comprising encapsulating polymer particles dispersed within the matrix of the ring and an active pharmaceutical ingredient separately dispersed in that matrix released the active pharmaceutical ingredient at a rate closer to zero order as compared to a matrix which did not comprise encapsulating polymer particles. Accordingly, changes in release profile must be considered when designing delivery devices of the present invention.

The present invention further relates to a surface coating for delivery devices comprising an anionic or nonionic hydrophilic polymer or polymers to minimize bio-interaction. For example, a coating of polyethylene glycol may be applied to a delivery device to inhibit adhesion of endogenous proteins and microbial growth to the device. Additional examples of polymers useful as surface coatings include, but are not limited to, poly(vinyl pyrrolidone, polyvinyl alcohol, PEO, and PEO-PPO copolymers, poly (acrylic acid), poly(methacrylic acid), and poly(styrene sulfonate). Also see springerlink with the extension .com/content/t234483257116u1q/ of the world wide web. In a preferred embodiment, this surface coating is applied to a delivery device described herein. Application of a coating to the delivery device of the present invention provides the advantage of improved safety. Further, the coating can be selected to provide for more reliable long term activated pharmaceutical ingredient release. For example, a hydrophobic matrix containing a hydrophilic active pharmaceutical ingredient can be coated with a hydrophilic coating to provide a molecular layer of water around the ring to aid in diffusion of the active pharmaceutical ingredient. In this embodiment, the coating provides a micro-environment to facilitate the transfer of the active pharmaceutical ingredient.

Figure 2:
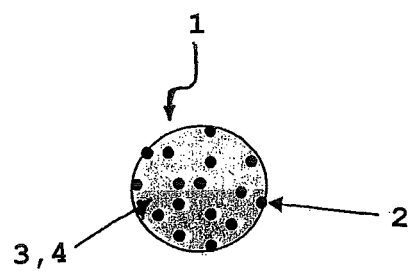
FIG. 2 is a cross-sectional view of the matrix of FIG. 1 and shows dispersion of the encapsulated active pharmaceutical ingredients throughout the matrix.

As shown in FIGS. 1 and 2, the delivery devices of the present invention are particularly well-suited to vaginal rings. Release from the vaginal ring device of the present invention is diffusion controlled. In a preferred embodiment, vaginal rings produced in accordance with the present invention will deliver the active pharmaceutical ingredient or active pharmaceutical ingredients at a rate comparable to existing technologies. Further, vaginal rings produced in accordance with present invention are expected to be useful for delivery of at least two or more active pharmaceutical ingredients dispersed in the matrix material at acceptable rates for at least 10 days, preferably 90 days. As shown in FIGS. 1 and 2, a vaginal ring 1 with two or more active pharmaceutical ingredients may comprise a first encapsulated active pharmaceutical ingredient 2 dispersed in the matrix 3 and a second non-encapsulated active pharmaceutical ingredient 4 added to the matrix material. Alternatively, the delivery device may comprise more than one encapsulated active pharmaceutical ingredient dispersed in the matrix material and/or one or more particle-bound active pharmaceutical ingredients. The matrix materials used in this vaginal ring embodiment of the present invention are flexible for ease in insertion and comfort during intercourse. Further, the matrix materials can be eco-friendly as they are either biodegradable and/or combustible. Manufacture of vaginal rings in accordance with the present invention is cost-efficient.

In this embodiment of the delivery device of the present invention depicted in FIGS. 1 and 2, dispersion of an encapsulated hydrophobic active pharmaceutical ingredient or active pharmaceutical ingredients in a hydrophobic non-degradable matrix material results in a delivery device wherein the active pharmaceutical ingredient or active pharmaceutical ingredients must first pass through the encapsulation material much the same way an active pharmaceutical ingredient passes through the core in a two-part standard ring. An advantage of the delivery device of the present invention is that there is no need to make two-part rings.

The vaginal ring depicted in FIGS. 1 and 2 is a smooth ring. However, vaginal rings of the present invention may also have an irregular surface with, for example, dimples or divets in the surface of the ring to increase surface area. In one embodiment, these dimples or divets serve as surface pockets that are filled with a second active pharmaceutical ingredient-containing matrix. In this embodiment, the ring itself releases one active pharmaceutical ingredient while the dimples or divets release another active pharmaceutical ingredient. The matrix in the dimples or divets may or may not be degradable. In this embodiment, encapsulated and/or particle-bound active pharmaceutical ingredients may or may not be present in the ring body.

The same particle-in-device approach used to produce vaginal rings can be used to produce films. In this embodiment of a delivery device of the present invention, encapsulated active pharmaceutical ingredients are dispersed in a film-shaped matrix. Matrix materials for the films are preferably degradable. Films of the present invention comprising a degradable matrix material are particularly useful for oral delivery of one or more encapsulated active pharmaceutical ingredients. In this embodiment, the film dissolves, for example in a subject's mouth, upon administration, thereby releasing the encapsulated active pharmaceutical ingredients to either adhere to the oral mucosa or be swallowed. The encapsulation material may provide bioadhesive properties or may simply be taste masking for active pharmaceutical ingredients that are not palatable but need to be delivered in a fast dissolving oral film. Alternatively, or in addition, the films may comprise one or more active pharmaceutical ingredients bound to particles, which upon dissolution of the film are swallowed. Films of the present invention are also useful for nasal and/or rectal delivery.

Examples of encapsulation materials expected to exhibit bioadhesive properties include, but are not limited to, compositions that are able to interact with negatively charged tissue cells or mucus films such as, but not limited to, cationic compositions. Active pharmaceutical ingredients encapsulated with these materials can be produced, for example, by the melt-chill encapsulation process described herein, using a cationic polymeric dispersant as a co-emulsifier in addition to the primary emulsion-forming emulsifier. Examples of cationic polymeric dispersants useful in this method include, but are not limited to, chitosan, poly (N,N dimethylaminomethacrylate), poly(2-vinyl pyridine), polyacrylamide, protamine, and poly(lysine). Alternatively bioadhesive encapsulated active pharmaceutical ingredients can be made using a low molecular weight cationic surfactant such as cetyl trimethyl ammonium bromide. Other bioadhesive compositions suitable for encapsulating hydrophilic active pharmaceutical ingredients may be made from natural hydrogel polymers such as gelatin, carageenan, alginate or chitosan. In this embodiment the active pharmaceutical ingredient and the polymer are both dissolved in water along with a crosslinking agent, for example, formalin for gelatin and chitosan. Particles of encapsulated active pharmaceutical ingredient are formed by, for example, spray drying the solution. As the sprayed droplets dry and shrink, they are crosslinked by the crosslinking agent to entrap the active pharmaceutical ingredients and prevent their redissolution, while allowing for their rehydration and adherence upon application to a moist surface such as a mucosal surface of the oral, rectal or nasal cavity.

Taste masking encapsulating materials for a non-palatable active pharmaceutical agent, for example, cod liver oil, can be prepared in accordance with methods described herein or known in the art with a better tasting encapsulating material which effectively masks the inherent taste of the non-palatable active pharmaceutical agent.

The delivery devices of the present invention are useful in administering one or more active pharmaceutical ingredients to a subject. Preferred subjects are mammals. More preferred subjects are humans. A delivery device of the present invention can be administered to a subject by various routes in accordance with the shape of the matrix material. For example, a delivery device with a vaginal ring-shaped matrix is administered by insertion of the delivery device into the vaginal lumen; a delivery device with a stent shaped matrix is administered by insertion of the stent into the vasculature of the subject; and a delivery device with a film shaped matrix is administered, e.g. orally, rectally or nasally via placement in oral, rectal or nasal cavity of the subject.

The following nonlimiting example is provided to further illustrate the present invention.

EXAMPLE

Example 1

Vaginal Ring Production

Vaginal rings were manufactured using injection molding. The ring matrix is either melted, as in the case of EVA, or catalytically formed from an elastomer, as with silicones. EVA vaginal rings were molded in a two-part aluminum mold. The rings were slightly smaller in diameter than the vaginal rings of Akzo Nobel. A target loading of 50 mg of active pharmaceutical ingredient is likely, which is about 1% by weight of active pharmaceutical ingredient. However, content of active pharmaceutical ingredient is ultimately determined by application and may vary substantially. Silicone rings are made in a similar mold.

Example 2

Melt-Chill Production of Bioadhesive Particles for a Film Delivery Device

Yellow carnauba, used as the particle encapsulation material, is melted along with the active pharmaceutical ingredient to form a single phase, and emulsified into a solution mixture of 1% Brij700 non-ionic emulsifier and 1% chitosan in 1% acetic acid (to dissolve the chitosan). After emulsification the dispersion is cooled to form cationic particles containing the encapsulated active pharmaceutical ingredient.

What is claimed is:

1. A delivery device for an active pharmaceutical ingredient comprising:
   a solid, degradable or nondegradable, biocompatible matrix shaped into a vaginal ring or intrauterine device, an anastomosis ring, a stent-shaped matrix, a rod, a disc, a lens or a solid film;
   one or more active pharmaceutical ingredients; and
   an encapsulation material selected from the group consisting natural or synthetic waxes or wax-like materials, polymeric materials, naturally occurring gelling agents, and combinations thereof which encapsulates the one or more active pharmaceutical ingredients, wherein said encapsulated active pharmaceutical ingredients are dispersed as solid particles in the solid matrix.

2. The delivery device of claim 1 further comprising one or more non-encapsulated active pharmaceutical ingredients dispersed in the matrix.

3. The delivery device of claim 1 wherein the matrix is shaped to facilitate delivery of the active pharmaceutical ingredient to its site of therapeutic action.

4. The delivery device of claim 3 wherein the matrix is a nondegradable matrix shaped into a vaginal ring.

5. The delivery device of claim 4 wherein the vaginal ring is smooth.

6. The delivery device of claim 4 wherein the vaginal ring has an irregular surface to increase surface area of the vaginal ring.

7. The delivery device of claim 6 wherein the irregular surface of the vaginal ring is dimpled or divetted.

8. The delivery device of claim 7 wherein the dimples are filled with a second active pharmaceutical ingredient-containing matrix.

9. The delivery device of claim 3 wherein the matrix is a degradable or nondegradable matrix shaped into a stent.

10. The delivery device of claim 3 wherein the matrix is a degradable matrix shaped into a solid film.

11. The delivery device of claim 1 further comprising a surface coating of one or more anionic or nonionic hydrophilic polymers applied to the delivery device to minimize bio-interaction.

12. A method for delivery of one or more active pharmaceutical ingredients to a subject comprising administering to the subject a delivery device of claim 1.

* * * * *